United States Patent

Yamazaki et al.

[11] Patent Number: 5,958,978
[45] Date of Patent: Sep. 28, 1999

[54] SPECIFIC CYCLOOXYGENASE 2 INHIBITOR AND ANTI-INFLAMMATORY AGENT

[75] Inventors: Ryuta Yamazaki; Takeshi Matsuzaki; Shusuke Hashimoto; Teruo Yokokura, all of Tokyo, Japan

[73] Assignees: Kabushiki Kaisha Yakult Honsha; Teikoku Hormone Mfg. Co., Ltd., both of Tokyo, Japan

[21] Appl. No.: 09/029,738

[22] PCT Filed: Sep. 11, 1996

[86] PCT No.: PCT/JP96/02583

§ 371 Date: Mar. 11, 1998

§ 102(e) Date: Mar. 11, 1998

[87] PCT Pub. No.: WO97/09977

PCT Pub. Date: Mar. 20, 1997

[30] Foreign Application Priority Data

Sep. 13, 1995 [JP] Japan ................................. 7-235142

[51] Int. Cl.$^6$ .................................................. A61K 31/19
[52] U.S. Cl. .................................................. 514/567
[58] Field of Search ................................. 514/567

[56] References Cited

FOREIGN PATENT DOCUMENTS

94/14977  7/1994  WIPO .

OTHER PUBLICATIONS

Moser et al., J. Med. Chem., 33(9), pp. 2358–2368, 1990.

*Primary Examiner*—Phyllis G. Spivack
*Attorney, Agent, or Firm*—Oblon, Spivak, McClelland, Maier & Neustadt, P.C.

[57] ABSTRACT

The invention relates to a specific cyclooxygenase 2 inhibitor which comprises, as an active ingredient, 2-(2,6-dichloro-4-hydroxyanilino)phenylacetic acid represented by the following formula (1):

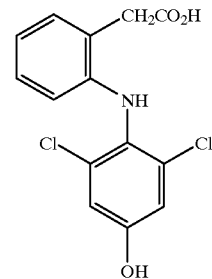

(1)

or a salt thereof, as an anti-inflammatory agent. The compound specifically inhibits cyclooxygenase 2 without inhibiting cyclooxygenase 1 activity and thus it is low in toxicity and safe.

2 Claims, No Drawings

SPECIFIC CYCLOOXYGENASE 2 INHIBITOR AND ANTI-INFLAMMATORY AGENT

This application is a 371 of PCT/JP96/02583, filed Sept. 11, 1996.

TECHNICAL FIELD

The present invention relates to a specific cyclooxygenase 2 inhibitor and an anti-inflammatory agent.

BACKGROUND ART

Cyclooxygenase is an enzyme that catalyzes the addition of two oxygen molecules to arachidonic acid isolated from a phospholipid in a cell membrane by phospholipase $A_2$ to synthesize prostaglandin $G_2$, and is a rate-determining enzyme in the synthetic system of prostaglandins such as prostaglandin $E_2$ and thromboxane $B_2$. Since Vane reported in 1971 that non-steroidal anti-inflammatory drugs such as aspirin and indomethacin inhibit the cyclooxygenase activity to inhibit the production of prostaglandin $E_2$, thereby manifesting an anti-inflammatory effect, many non-steroidal anti-inflammatory drugs have been developed by pharmaceutical companies. However, most of the non-steroidal anti-inflammatory drugs inhibit the production of not only prostaglandin $E_2$ in an inflammatory site but also prostaglandin $E_2$ having a mucosa-protecting effect in digestive tracts, so that they have a stomach and intestine-damaging effect, and this side effect offers a clinical problem.

In recent years, it has been reported that subtype enzymes exist in the cyclooxygenase. Cyclooxygenase 1 conventionally known always manifests itself in cells of the gastric mucosa, seminal vesicle, platelet and the like and is considered to participate in the maintenance of homeostasis in the living body. On the other hand, cyclooxygenase 2 newly discovered is induced by stimulating a cell participating in inflammation such as a macrophage or synovial cell by a cytokine or the like and is hence considered to participate in an inflammatory reaction. The non-steroidal anti-inflammatory drugs clinically used at present are considered to inhibit not only cyclooxygenase 2 but also the cyclooxygenase 1 activity, thereby bringing about an anti-inflammatory effect and at the same time inducing gastrointestinal disorders.

Therefore, it is expected to develop a drug specifically inhibiting the cyclooxygenase 2 activity as a novel anti-inflammatory agent.

Accordingly, it is an object of the present invention to provide a drug which has an effect of specifically inhibiting the cyclooxygenase 2 activity, and an anti-inflammatory agent scarcely having a stomach and intestine-damaging effect.

DISCLOSURE OF THE INVENTION

In view of the foregoing circumstances, the present inventors have carried out an extensive investigation. As a result, it has been found that 2-(2,6-dichloro-4-hydroxyanilino) phenylacetic acid or a salt thereof specifically inhibits cyclooxygenase 2, which catalyzes the synthesis of prostaglandin $E_2$ produced in an inflammatory site, without inhibiting the activity of cyclooxygenase 1 which catalyzes the synthesis of prostaglandin $E_2$ produced in the gastric mucosa or the like, and thus the use of this compound provides an excellent anti-inflammatory agent which scarcely causes any gastrointestinal disorders, thus leading to completion of the present invention.

According to the present invention, there is thus provided a specific cyclooxygenase 2 inhibitor which comprises, as an active ingredient, 2-(2,6-dichloro-4-hydroxyanilino) phenylacetic acid represented by the following formula (1):

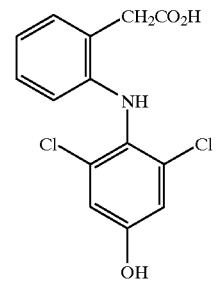

(1)

or a salt thereof.

According to the present invention, there is also provided an anti-inflammatory agent which comprises, as an active ingredient, 2-(2,6-dichloro-4-hydroxyanilino)-phenylacetic acid represented by the formula (1) or a salt thereof.

According to the present invention, there is further provided a specific cyclooxygenase 2 inhibitor composition which comprises 2-(2,6-dichloro-4-hydroxyanilino)-phenylacetic acid represented by the formula (1) or a salt thereof and a pharmaceutically acceptable carrier.

According to the present invention, there is still further provided an anti-inflammatory agent composition which comprises 2-(2,6-dichloro-4-hydroxyanilino)-phenylacetic acid represented by the formula (1) or a salt thereof and a pharmaceutically acceptable carrier.

According to the present invention, there is yet still further provided use of 2-(2,6-dichloro-4-hydroxyanilino) phenylacetic acid represented by the formula (1) or a salt thereof for the preparation of a specific cyclooxygenase 2 inhibitor.

According to the present invention, there is yet still further provided use of 2-(2,6-dichloro-4-hydroxyanilino) phenylacetic acid represented by the formula (1) or a salt thereof for the preparation of an anti-inflammatory agent.

According to the present invention, there is yet still further provided a method of treating a disease caused by cyclooxygenase 2, which comprises administering an effective amount of 2-(2,6-dichloro-4-hydroxyanilino)-phenylacetic acid represented by the formula (1) or a salt thereof to a patient.

According to the present invention, there is yet still further provided a method of treating inflammation, which comprises administering an effective amount of 2-(2,6-dichloro-4-hydroxyanilino)phenylacetic acid represented by the formula (1) or a salt thereof to a patient.

BEST MODE FOR CARRYING OUT THE INVENTION 2-(2,6-Dichloro-4-hydroxyanilino)phenylacetic acid (hereinafter abbreviated as 4'-hydroxydiclofenac) represented by the formula (1) used in the specific cyclooxygenase 2 inhibitor according to the present invention is known as a main metabolite in blood of diclofenac. However, this compound (1) is not known at all to have an anti-inflammatory effect.

As a process for the preparation of 4'-hydroxy-diclofenac, there may be used any known process. The compound can be efficiently prepared, for example, in accordance with the following process:

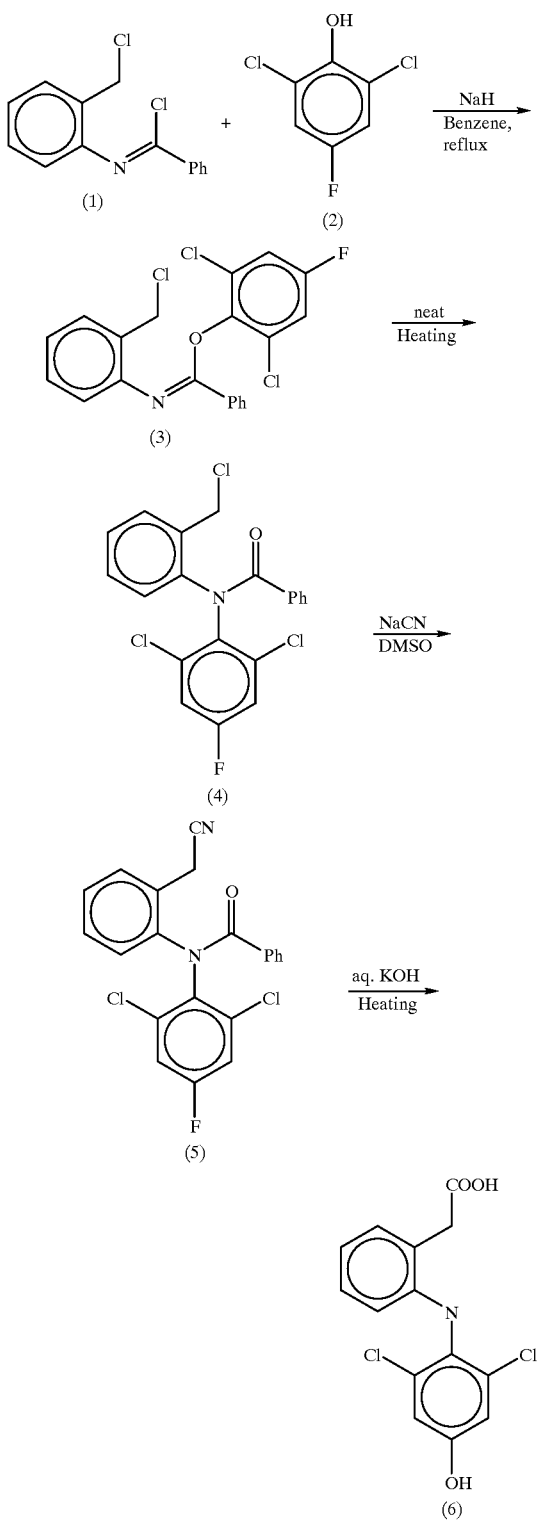

any solvent to obtain a rearranged product (4). This compound (4) is converted into a cyanide (5) in accordance with a method known per se in the art, and the cyanide (5) is then hydrolyzed with a concentrated alkali. The hydrolyzate is neutralized, and is then isolated and purified by column chromatography on ODS.

The salt of 4'-hydroxydiclofenac is preferably an alkali metal salt, particularly, the sodium salt.

No particular limitation is imposed on the specific cyclooxygenase 2 inhibitor or anti-inflammatory agent according to the present invention. However, it is preferably used for a patient suffering from any of various inflammations such as chronic articular rheumatism.

When the specific cyclooxygenase 2 inhibitor or anti-inflammatory agent according to the present invention is administered to a patient, the preferable dose thereof varies according to the age and condition of the patient, and the like. However, it is preferably administered in a dose of generally 20 to 200 mg per day for an adult in terms of the active ingredient at once or in several portions. No particular limitation is imposed on the administration route thereof. Examples thereof include oral administration, injection administration and rectal administration.

The specific cyclooxygenase 2 inhibitor or anti-inflammatory agent according to the present invention includes the above-described 4'-hydroxydiclofenac or the salt thereof as an active ingredient and besides may contain any optional ingredients useful for the formulation of preparations, which are routinely used in medicinal compositions, in any suitable proportions. Examples of the optional ingredients include excipients, extending agents, binders, wetting agents, disintegrators, surfactants, lubricants, dispersing agents, buffers, preservatives, taste corrigents, perfume bases and coating agents.

Examples of preparation forms for the oral administration include powder, granules, tablets, sugarcoated tablets, capsules and ampoules, while examples of injection preparations include subcutaneous injections, intramusclar injections and intravenous injections.

EXAMPLES

The present invention will hereinafter be described more specifically by the following Examples which are included merely to illustrate the present invention, and do not limit the invention.

Example 1
(Specific Inhibitory Effect on Cyclooxygenase)

Added to 2 $\mu$l of a solution of 4'-hydroxydiclofenac, diclofenac or indomethacin [dissolved in DMSO (dimethyl sulfoxide); end concentration: 0.01–100 $\mu$M] were 100 $\mu$l of a 50 mM tris-hydrochloric acid buffer solution (pH: 8.0) containing 1 mM epinephrine, 2 mM phenol, and 200 $\mu$g/ml of sheep seminal vesicle microsome (cyclooxygenase 1) or 5 units of cyclooxygenase 2, and the mixture was incubated at 37° C. for 5 minutes. After the incubation, 2 $\mu$l of a 5 mM solution of arachidonic acid (dissolved in ethanol) were added (end concentration: 100 $\mu$M), followed by incubation for additional 5 minutes. After the incubation for 5 minutes, 10 $\mu$l of a 22 mM solution of ferrous chloride were added, and the resultant mixture was cooled down to 0° C. to stop the reaction. After stopping the reaction, the reaction mixture was centrifuged at 10,000×g for 5 minutes to determine the amount of prostaglandin $E_2$ in the supernatant liquid thereof in accordance with the enzyme immunoassay. The cyclooxygenase-inhibiting effect of each test agent was More specifically, commercially available 2-aminobenzyl alcohol is N-acylated with a stoichiometric amount of benzoyl chloride into a benzoamide, and this product is then boiled under reflux in thionyl chloride to obtain an imidoyl chloride (1). The imidoyl chloride is then reacted with commercially available 2,6-dichloro-4-fluorophenol (2) to convert it into an imidate (3). The imidate is heated (for 30 minutes at 250° C.; Chapman rearrangement) without using determined by the average value of the amounts of prostaglandin $E_2$ produced, which were obtained by repeating the above process twice, and the amount of prostaglandin $E_2$ produced by using DMSO in place of the test agent to conduct the same treatment as described above. The percent inhibitions of cyclooxygenases 1 and 2 at the individual concentrations are shown in Table 1 and Table 2, respectively.

TABLE 1

Percent inhibition of cyclooxygenase 1 (%)

|  | 0.01 | 0.1 | 1 | 10 | 100 ($\mu$M) |
|---|---|---|---|---|---|
| 4'-Hydroxydiclofenac | 0 | 0 | 13 | 3 | 15 |
| Indomethacin | 15 | 30 | 40 | 55 | 85 |
| Diclofenac | 25 | 25 | 38 | 57 | 87 |

TABLE 2

Percent inhibition of cyclooxygenase 2 (%)

|  | 0.01 | 0.1 | 1 | 10 | 100 ($\mu$M) |
|---|---|---|---|---|---|
| 4'-Hydroxydiclofenac | 21 | 18 | 22 | 82 | 90 |
| Indomethacin | 25 | 28 | 50 | 88 | 90 |
| Diclofenac | 20 | 40 | 80 | 88 | 90 |

As apparent from Table 1 and Table 2, Inhibitory effects on cyclooxygenase 1 and cyclooxygenase 2 are recognized in indomethacin and diclofenac. On the other hand, no inhibitory effect on cyclooxygenase 1 is recognized in 4'-hydroxydiclofenac, and only an inhibitory effect on the cyclooxygenase 2 activity is recognized.

Example 2
(Effect of 4'-Hydroxydiclofenac on Production of Prostaglandin $E_2$ by Stimulation of Human Synovial Cell by IL-1$\beta$)

Synovial tissue obtained from a patient suffering from chronic articular rheumatism was placed in a Petri dish, cut and shredded, to which a 0.2% solution of collagenase was added. The mixture was left over for 2 hours under conditions of 5% $CO_2$ and 37° C. An equiamount of a 0.25% solution of trypsin was further added, and the resultant mixture was left over for 2 hours. After cells isolated were collected and centrifuged (170 ×g, 10 minutes) to remove the supernatant liquid thereof, a medium [obtained by adding 10% FCS (fetal calf serum), 2 mM glutamine, 100 U/ml of penicillin, 100 $\mu$g/ml of streptomycin and 25 ng/ml of Fungizone to DMEM (Dulbecco modified minimum essential medium)] was added to the cells to wash them once. The cells were suspended in the medium, and the suspension was poured into a Petri dish and cultured under conditions of 5% $CO_2$ and 37° C. Cells adhered to the bottom of the Petri dish were provided as synovial cells. The cells (1×105 cells/ml) were poured in 1-ml portions into wells of a 24-well plate and cultured under conditions of 5% $CO_2$ and 37° C. After the cells were proliferated to an extent that they covered almost the entire surface of each well, the medium was changed to an SFM-101 medium (product of Nissui Seiyaku K.K.) containing 1% FCS. Added to an assigned well were 5 $\mu$l (end concentration: 0.001-100 $\mu$M) of a solution of 4'-hydroxydiclofenac, indomethacin or diclofenac. Furthermore, 10 $\mu$l (end concentration: 200 pg/ml) of a solution of IL-1$\beta$ and 10 $\mu$l (end concentration: 10 $\mu$M) of arachidonic acid were added to conduct culture for 22 hours under conditions of 5% $CO_2$ and 37° C. After the culture, the supernatant liquid thereof was collected and filtered through a membrane filter (pore size: 0.22 $\mu$m, MILLIPORE), thereby determining the amount of prostaglandin $E_2$ in the filtrate in accordance with the enzyme immunoassay. The effect of each test agent on the production of prostaglandin $E_2$ by the human synovial cells was determined by the average value of the amounts of prostaglandin $E_2$ produced, which were obtained by repeating the above process 3 times, and the amount of prostaglandin $E_2$ produced by using DMSO in place of the test agent to conduct the same treatment as described above. The results are shown in Table 3.

TABLE 3

Percent inhibition of prostaglandin $E_2$ (%)

|  | 0.001 | 0.01 | 0.1 | 1 | 10 | 100 ($\mu$M) |
|---|---|---|---|---|---|---|
| 4'-Hydroxydiclofenac | −3 | 0 | 35 | 100 | 100 | 100 |
| Indomethacin | −3 | 5 | 62 | 100 | 100 | 100 |
| Diclofenac | 14 | 61 | 99 | 100 | 100 | 100 |

As apparent from the results shown in Table 3, the inhibitory effect of 4'-hydroxydiclofenac on prostaglandin $E_2$ is almost comparable to indomethacin. It has been reported that in inflammation-related cells such as the synovial cell, the manifestation of cyclooxygenase 2 is induced by stimulating the cells by IL-1$\beta$ without affecting the manifestation of cyclooxygenase 1. Therefore, 4'-hydroxydiclofenac is considered to inhibit cyclooxygenase 2 also in the cell-level test.

Referential Example
(Effect of 4'-Hydroxydiclofenac on Production of Thromboxane $B_2$ in Platelet)

Fresh blood [adding 1 volume of ACD (acid-citrate dextrose; consisting of 65 mM citric acid, 85 mM sodium citrate and 110 mM glucose) to 9 volumes of the blood] collected from the heart of a rabbit under Nembutal anesthesia was centrifuged at 200 ×g for 10 minutes to collect the supernatant liquid thereof. The supernatant liquid was centrifuged at 700 ×g for 10 minutes, and precipitated platelets were suspended in an isotonic trishydrochloric acid buffer solution [50 mM tris(hydroxymethyl)aminomethane, 150 mM NaCl, 1 mM EDTA (ethylenediaminetetraacetic acid) and 5 mM glucose; pH: 7.2]. The suspension was further centrifuged at 700 ×g for 10 minutes and washed. After washed again, precipitated platelets were suspended in an isotonic HEPES (2-[4-(2-hydroxyethyl)-1-piperazinyl]ethanesulfonic acid) buffer solution (10 mM HEPES, 145 mM NaCl, 5 mM KCl and 5.5 mM glucose; pH: 7.4) to adjust the concentration of the platelets to 3×10$^9$ cells/ml. The thus-adjusted platelet suspension was poured in 1-ml portions into test tubes. To one of the test tubes, were added 5 Al (end concentration: 0.001-100 $\mu$M) of a solution of 4'-hydroxydiclofenac, indomethacin or diclofenac, and the test tube was preincubated for 30 minutes at 37° C. After the incubation, 10 $\mu$l (end concentration: 2 mM) of 200 mM $CaCl_2$ and 5 $\mu$l (end concentration: 5 $\mu$M) of 1 mM arachidonic acid were added, followed by incubation for additional 5 minutes. After the incubation, the test tube was transferred to an ice bath to stop the reaction. The test tube was centrifuged at 1,500 ×g and 4° C. for 10 minutes. After the supernatant liquid thereof was filtered through a membrane filter (pore size: 0.22 $\mu$m, MILLIPORE), the amount of thromboxane $B_2$ in the filtrate was determined in accordance with the enzyme immunoassay. The effect of each test agent on the production of thromboxane $B_2$ in the platelet was determined by the average value of the amounts of thromboxane $B_2$ produced, which were obtained by repeating the above process 3 times, and the amount of thromboxane $B_2$ produced by using DMSO in place of the test agent to conduct the same treatment as described above. The results are shown in Table 4.

TABLE 4

| | Percent inhibition of thromboxane $B_2$ (%) | | | | | |
|---|---|---|---|---|---|---|
| | 0.001 | 0.01 | 0.1 | 1 | 10 | 100 ($\mu$M) |
| 4'-Hydroxydiclofenac | −25 | −25 | 0 | 7 | 15 | 77 |
| Indomethacin | 2 | 50 | 76 | 77 | 78 | 78 |
| Diclofenac | 46 | 70 | 68 | 77 | 93 | 99 |

As apparent from the results shown in Table 4, an inhibitory effect on the production of thromboxane $B_2$ is recognized in indomethacin and diclofenac. On the other hand, the inhibitory effect of 4'-hydroxydiclofenac is clearly weak compared with indomethacin. It has been known that thromboxane $B_2$ is produced in the platelet by the cyclooxygenase 1 activity. Therefore, the inhibitory effect of 4'hydroxydiclofenac on cyclooxygenase 1 is considered to be weak also in the cell-level test.

Example 3

The following ingredients were mixed, and the mixture was tableted.

TABLE 5

| 4'-Hydroxydiclofenac | 100 mg |
|---|---|
| Lactose | 100 mg |
| Potato starch | 39 mg |
| Microcrystalline cellulose | 30 mg |
| Synthetic aluminum silicate | 30 mg |
| Calcium stearate | 1 mg |
| Total amount (per tablet) | 300 mg |

As described above, 4'-hydroxydiclofenac specifically inhibits cyclooxygenase 2, so that the use of this compound as an anti-inflammatory agent has an anti-inflammatory effect almost without causing any side effects such as gastrointestinal disorders.

Industrial Applicability

The specific cyclooxygenase 2 inhibitor according to the present invention specifically inhibits cyclooxygenase 2, which catalyzes the synthesis of prostaglandin $E_2$ produced in an inflammatory site, without inhibiting the activity of cyclooxygenase 1 which catalyzes the synthesis of prostaglandin $E_2$ produced in the gastric mucosa or the like.

Besides, the use of the anti-inflammatory agent comprising 4'-hydroxydiclofenac or the salt thereof as an active ingredient has an excellent anti-inflammatory effect without causing any gastrointestinal disorders as side effects. This agent is a main metabolite in blood of diclofenac which is already in clinical use as a non-steroidal anti-inflammatory agent, and is hence low in toxicity and safe.

We claim:

1. A method of treating a disease caused by cyclooxygenase 2, which comprises administering an effective amount of 2-(2,6-dichloro-4-hydroxyanilino)-phenylacetic acid represented by the following formula (1)

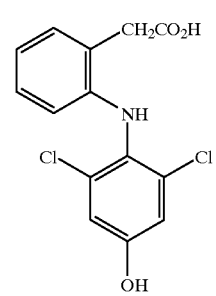

(1)

or a salt thereof to a patient.

2. A method of treating inflammation by inhibiting cyclooxygenase 2 activity without inhibiting activity of cyclooxygenase 1, which comprises administering an effective amount of 2-(2,6-dichloro-4-hydroxyanilino)-phenylacetic acid represented by the following formula (1)

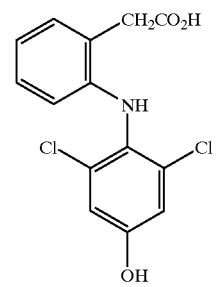

(1)

or a salt thereof to a patient.

* * * * *